(12) United States Patent
Lalonde et al.

(10) Patent No.: US 11,957,396 B2
(45) Date of Patent: Apr. 16, 2024

(54) CONTROL METHOD FOR A ONE BALLOON FITS ALL IN AUTOMATED MODE

(71) Applicant: Medtronic CryoCath LP, Toronto (CA)

(72) Inventors: Jean-Pierre Lalonde, Candiac (CA); Wlodzimierz Sadzynski, Chateauguay (CA); Nicolas Coulombe, Montreal (CA)

(73) Assignee: Medtronic CryoCath LP, Toronto (CA)

( * ) Notice: Subject to any disclaimer, the term of this patent is extended or adjusted under 35 U.S.C. 154(b) by 759 days.

(21) Appl. No.: 16/838,133

(22) Filed: Apr. 2, 2020

(65) Prior Publication Data

US 2021/0307804 A1    Oct. 7, 2021

(51) Int. Cl.
*A61B 18/02* (2006.01)
*A61B 18/00* (2006.01)

(52) U.S. Cl.
CPC ...... *A61B 18/02* (2013.01); *A61B 2018/0022* (2013.01); *A61B 2018/0212* (2013.01); *A61B 2018/0243* (2013.01); *A61B 2562/0247* (2013.01)

(58) Field of Classification Search
CPC .................. A61B 18/02; A61B 2018/0022
USPC .......................................................... 606/21
See application file for complete search history.

(56) References Cited

U.S. PATENT DOCUMENTS

| 4,781,677 | A | 11/1988 | Wilcox |
| 5,470,313 | A | 11/1995 | Crocker et al. |
| 7,081,112 | B2 | 7/2006 | Joye et al. |
| 2013/0345688 | A1 | 12/2013 | Babkin et al. |

(Continued)

FOREIGN PATENT DOCUMENTS

CN    110575251 A  * 12/2019   ......... A61B 18/1815

OTHER PUBLICATIONS

Olympus America, Balloons, Balloon Catheter, Multi-3V Extraction Balloon, http://medical.olympusamerica,com/products/balloons/multi-3v-extraction-balloon-b-v231p, 2 pages.

(Continued)

*Primary Examiner* — Nicole F Lavert
(74) *Attorney, Agent, or Firm* — Michael Best & Friedrich LLP

(57) ABSTRACT

Devices, systems, and methods for maintaining cryoballoon size, cryoballoon pressure, and/or coolant flow rate based on physical characteristics of the tissue to be ablated. In one embodiment, a cryoablation system comprises: a cryoablation device, the cryoablation device including: an expandable treatment element defining an interior chamber; and a pressure sensing system at least partially within the interior chamber; a fluid flow path including at least one valve that is in communication with at least one PID device; and a control unit including processing circuitry in communication with the pressure sensing system and the at least one PID device, the processing circuitry being configured to: determine a target pressure of the expandable treatment element based on a target size of the expandable treatment element; and determine a target flow rate of coolant through the fluid flow path based on the target pressure of the expandable treatment element.

22 Claims, 10 Drawing Sheets

(56) References Cited

U.S. PATENT DOCUMENTS

2016/0008049 A1* 1/2016 Mahrouche ............ A61B 18/02
                                                    606/21
2017/0042614 A1* 2/2017 Salahieh ............ A61M 25/1011
2018/0036057 A1   2/2018 Abboud et al.
2018/0310978 A1* 11/2018 Avitall .................. A61B 5/287

OTHER PUBLICATIONS

Conwinonline.com, Precision Air V6 Inflator, https://www.conwinonline.com/shop/precision-air-v6-inflator/, 3 pages.
International Search Report and Written Opinion dated Mar. 31, 2021, for corresponding International Application No. PCT/CA2021/050054; International Filing Date: Jan. 20, 2021 consisting of 11-pages.

* cited by examiner

CONTROL METHOD FOR A ONE BALLOON FITS ALL IN AUTOMATED MODE

CROSS-REFERENCE TO RELATED APPLICATION n/a.

FIELD

The present technology is generally related to cryoablating tissue with a cryoablation device having an expandable treatment element, as well as systems and methods for maintaining at least one of a balloon size, balloon pressure, and coolant flow rate based on physical characteristics of the tissue to be ablated.

BACKGROUND

Many medical procedures, such as ablation, angioplasty, dilation, and others are performed using catheters and other minimally invasive devices. Some procedures may require multiple devices and/or treatment steps. For example, an ablation procedure may involve creating a series of interconnecting lesions in order to electrically isolate tissue believed to be the source of an arrhythmia. To achieve this, a physician may use several different devices, each having ablation element(s) with different geometry and/or dimensions based on the procedure being performed and/or the anatomical variations between patients. Each device may have a unique geometry for creating a specific lesion pattern or size, with the multiple devices being sequentially removed and replaced to create the desired lesions or achieve the desired results. However, exchanging these various devices during a procedure can cause inaccuracies or movement in the placement and location of the distal tip relative to the tissue being treated, and may further add to the time required to perform the desired treatment. These potential inaccuracies and extended procedure time increase the risk to the patient undergoing treatment.

Additionally, some such minimally invasive devices include a balloon or other expandable element. However, these expandable elements often must be manufactured or constructed to have a particular shape or dimension for a specific application, and as such, any given catheter with an expandable element may be limited to use in situations where the fixed dimensions of the expandable element are appropriate. For example, an expandable element such as a balloon may have a fixed radius when inflated, making it only suitable for a procedure requiring such a dimension or where a particular vasculature may accommodate that radius. As such, multiple devices having varying fixed dimensions may be needed to successfully perform a desired treatment or to account for variations between patients.

Still further, it is typically desirable that minimally invasive devices are as small as possible so they may be navigated safely through the patient's vasculature. However, as size (for example, diameter) of the elongate body and coolant conduits within the device decreases, the flow of coolant through the device may become restricted. Under normal operating conditions, pressure remains high within the expandable element (typically around +18 psig at nominal coolant flow) and cannot be reduced to a lower pressure near atmospheric pressure (−2 psig to +5 psig), even with a very efficient vacuum system. Thus, the restriction of coolant flow not only limits the cooling power of the device but also presents a risk of rupture in the expandable element due to excessive expansion pressure.

SUMMARY

The techniques of this disclosure generally relate to the cryoablation of tissue with a cryoablation device having an expandable treatment element, as well as systems and methods for maintaining at least one of a balloon size, balloon pressure, and coolant flow rate based on physical characteristics of the tissue to be ablated. In one embodiment, a cryoablation system comprises: a cryoablation device, the cryoablation device including: an expandable treatment element defining an interior chamber; and a pressure sensing system at least partially within the interior chamber; a fluid flow path, the fluid flow path including at least one valve; and a control unit, the control unit including processing circuitry in communication with the pressure sensing system, the processing circuitry being configured to: determine a target pressure of the expandable treatment element based on a target size of the expandable treatment element; and determine a target flow rate of coolant through the fluid flow path based on the target pressure of the expandable treatment element.

In one aspect of the embodiment, the fluid flow path includes a coolant delivery conduit and a coolant recovery conduit. In one aspect of the embodiment, the coolant delivery conduit includes a first valve. In one aspect of the embodiment, the coolant recovery conduit includes a second valve.

In one aspect of the embodiment, the processing circuitry is further configured to: determine at least one flow rate setpoint and adjust the at least one valve to maintain a flow rate of coolant through the fluid flow path at the target flow rate.

In one aspect of the embodiment, the processing circuitry is configured to determine the target flow rate of coolant through the fluid flow path based on the target pressure of the expandable treatment element and a target cooling capacity of the expandable treatment element. In one aspect of the embodiment, the target cooling capacity is one at which the expandable treatment element is operable to ablate tissue. In one aspect of the embodiment, the target pressure is at most 10 psig.

In one aspect of the embodiment, the processing circuitry is further configured to receive the target size of the expandable treatment element as input data from a user. In one aspect of the embodiment, the target size of the expandable treatment element is between approximately 25 mm and approximately 38 mm.

In one aspect of the embodiment, the pressure sensing system includes: a pressure sensor; and a pressure sensor extension tube in fluid communication with the pressure sensor.

In one aspect of the embodiment, the pressure sensing system further includes a flow meter in fluid communication with the fluid flow path.

In one aspect of the embodiment, the cryoablation device further includes: an elongate body having a distal portion and a proximal portion opposite the distal portion, the expandable treatment element being coupled to the distal portion; and a handle coupled to the proximal portion, the pressure sensor being located within the handle and the pressure sensor extension tube extending through the elongate body such that at least a portion of the pressure sensor extension tube is located within the interior chamber of the expandable treatment element.

In one embodiment, a cryoablation system comprises a control unit including processing circuitry, the processing circuitry being configured to: receive a target size of an expandable treatment element of a cryoablation device as input data from a user; determine a target pressure of the expandable treatment element based on a target size of the expandable treatment element; and determine a target flow rate of coolant through the fluid flow path based on the target pressure of the expandable treatment element and a target cooling capacity of the expandable treatment element.

In one aspect of the embodiment, wherein the target pressure is at most 10 psig.

In one aspect of the embodiment, the target size of the expandable treatment element is between approximately 25 mm and approximately 38 mm.

In one aspect of the embodiment, the target cooling capacity is one at which the expandable treatment element is operable to ablate tissue.

In one embodiment, a method of cryoablating tissue comprises: inputting into a control unit a target balloon size, the control unit including processing circuitry, the target balloon size being the target size of a balloon of a cryoablation device; determining, with the processing circuitry, a target balloon pressure based on the target balloon size; determining, with the processing circuitry, a target coolant flow rate based on the target balloon pressure and a target cooling capacity of the balloon; delivering coolant through a fluid flow path to the balloon; maintaining the target coolant flow rate through a cryoablation procedure, such that the target balloon size, target balloon pressure, and target cooling capacity are maintained; and cryoablating tissue with the balloon.

In one aspect of the embodiment, the processing circuitry is in communication with a valve in the fluid flow path, the step of maintaining the target coolant flow rate including: determining, with the processing circuitry, at least one flow rate setpoint; and automatically adjusting the valve to maintain a flow of coolant through the fluid flow path at the target flow rate. In one aspect of the embodiment, the method further comprises: measuring a pressure within the balloon with a pressure sensing system; comparing the measured pressure with the target balloon pressure; and automatically adjusting the flow of coolant through the fluid flow path to adjust the measured pressure to the target balloon pressure.

In one aspect of the embodiment, the method further comprises: positioning the balloon at least partially within a hollow anatomical structure, the target balloon size being a size that allows the balloon to be in contact with an inner surface of the hollow anatomical structure; and cryoablating the inner surface of the hollow anatomical structure.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

The systems, devices, and methods of the present disclosure generally provide efficient cooling of tissue while minimizing the risk of balloon or treatment element rupture or burst. In some embodiments, the present disclosure provides a cryoablation device having an elongate body with an increased cross-sectional area, which allows for low expansion pressure, such as approximately atmospheric pressure, under normal operating coolant flow conditions. This, in turn, reduces the effect the coolant flow has on the balloon expansion pressure. Further, in some embodiments the pressure disclosure provides a cryoablation system that includes at least one valve in a coolant recovery conduit and a sensing system to monitor expansion pressure within the balloon and to control the expansion pressure independently of coolant flow. Thus, the devices and systems discussed herein allow for the maintenance of a "soft balloon," or a balloon that is maintained as a low inflation pressure, such as a pressure that is equal to or approximately equal to atmospheric pressure (for example, between −2 psig and +5 psig), to make the balloon more compliant for it to adapt to the anatomy of the treatment site at low balloon inflation pressure (rather than the anatomy stretching or conforming to a balloon having a higher inflation pressure and larger size) and/or to control the size of the inflated balloon. For example, although a soft balloon with a low inflation pressure may be appropriate in many cases, in some cases a balloon having a larger inflation size and greater inflation pressure may be desired, such as when the treatment site includes a larger area.

Figure 1:
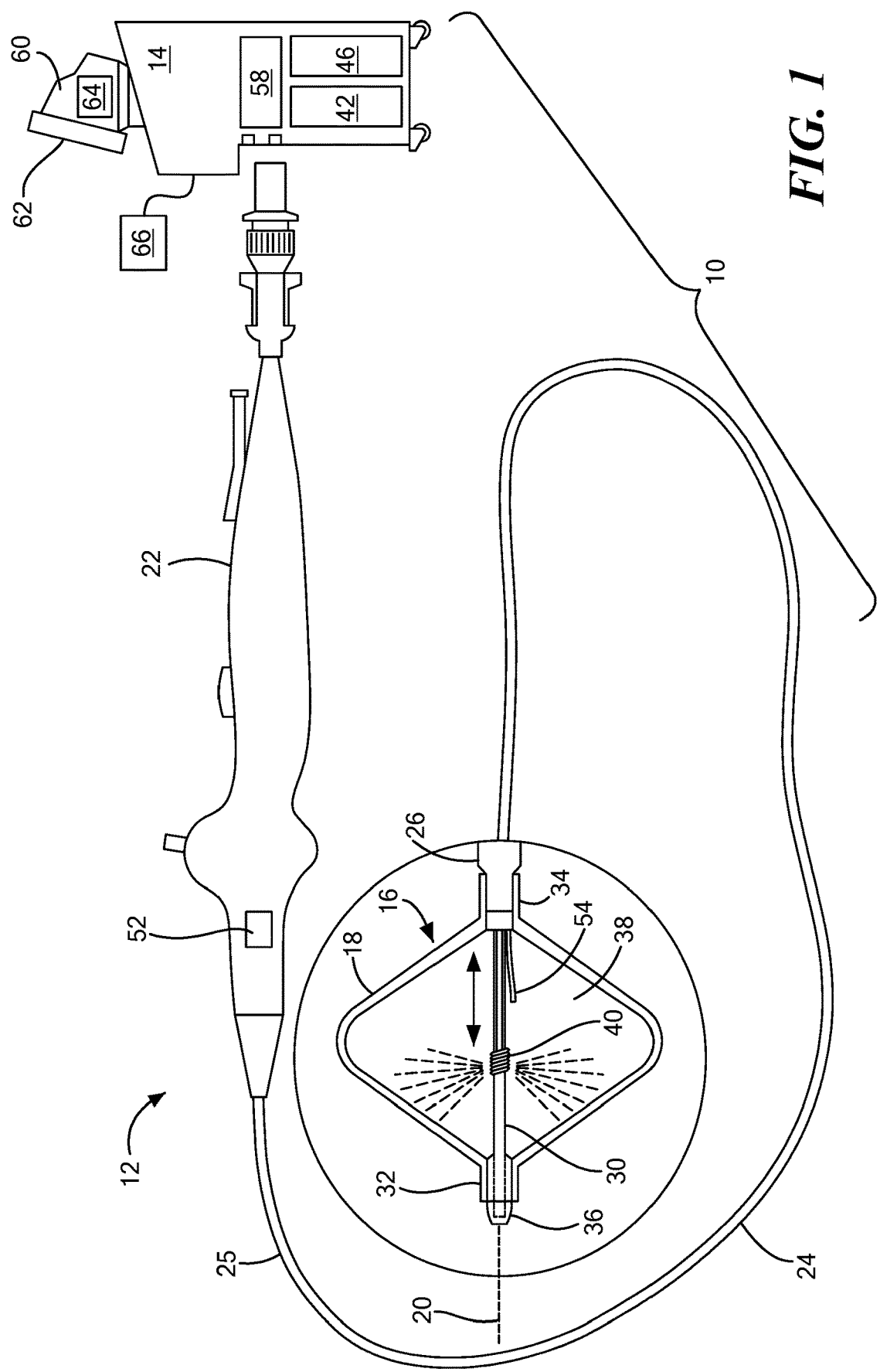
FIG. 1 shows an exemplary medical system in accordance with the present disclosure, the medical system including a cryoablation device with a balloon.

Referring now to FIG. 1, an exemplary medical system 10 for cryoablation is shown. In one embodiment, the medical system 10 generally includes a treatment device, such as a cryoablation device 12, and a control unit 14 in communication with the cryoablation device 12. In one embodiment, the cryoablation device 12 includes one or more treatment elements 16. Although the cryoablation device 12 is described herein as being operable to reduce the temperature of target tissue (for example, cardiac, renal, pulmonary, and/or other tissue) to cause cryoablation of that tissue, it will be understood that the cryoablation device may also be used with one or more additional modalities, such as radiofrequency (RF) ablation, pulsed field ablation, ultrasound ablation, microwave ablation, or the like. Additionally, the cryoablation device 12 may be used for treatment, denervation, or nerve modulation.

Continuing to refer to FIG. 1, in one embodiment, the treatment element(s) 16 are configured to deliver cryogenic therapy, and may further be configured to deliver RF energy, pulsed field ablation energy, or the like for energetic transfer with an area of tissue and, in such an embodiment, the cryoablation device 12 may include one or more electrodes at various locations on the cryoablation device 12 (for example, at or on the distal tip, on the treatment element 16, or the like). In one embodiment, the treatment element(s) 16 include one or more balloons 18 within which a coolant is circulated in order to reduce the temperature of the balloon (s) 18 and, as a result, to reduce the temperature of tissue that is in contact with and/or adjacent to the balloon(s) 18. Additionally, in some embodiments the balloon(s) 18 include other thermally and/or electrically-conductive elements, such as one or more electrodes (not shown) in communication with the control unit 14. Further, although one balloon 18 is shown in the figures, it will be understood that the medical device 12 may include more than one balloon 18 positioned next to each other and/or layered on top of each other. For example, the treatment element 16 may include a first balloon positioned within a second balloon (not shown).

Figure 2:
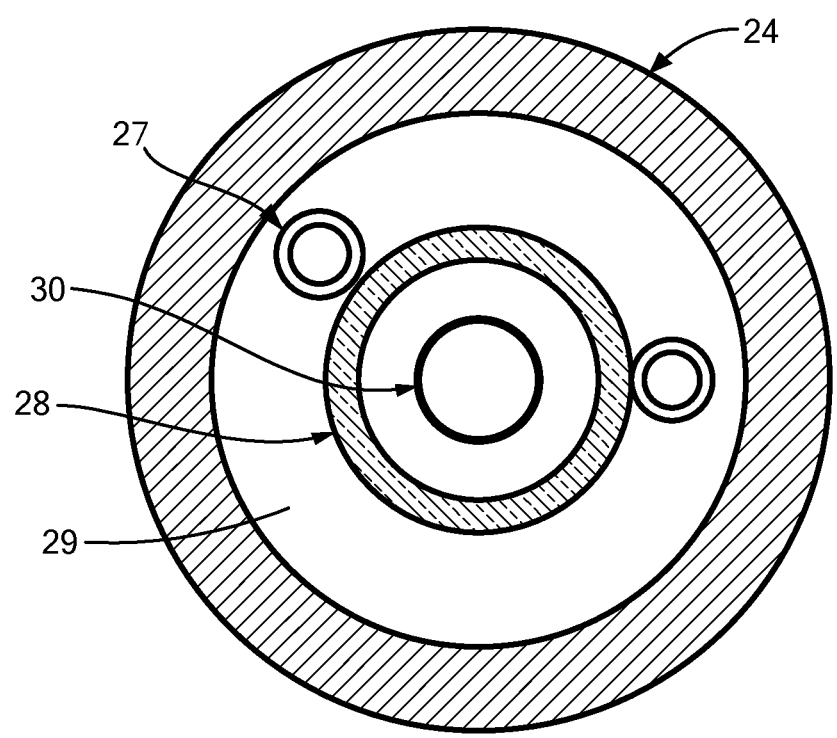
FIG. 2 shows a cross-sectional view of an elongate body of the cryoablation device of FIG. 1, in accordance with the present disclosure.

Continuing to refer to FIG. 1, and with reference to FIG. 2, in one embodiment, in addition to the treatment element (s) 16, the cryoablation device 12 also defines a longitudinal axis 20 and generally includes a handle 22 and an elongate body 24 coupled to the handle 22. The elongate body 24 is sized and configured to be passable through a patient's vasculature and/or positionable proximate to a tissue region for diagnosis or treatment, such as a catheter, sheath, or intravascular introducer. The elongate body 24 includes a proximal portion 25 coupled to the handle 22, a distal portion 26 opposite the proximal portion 25, and one or more lumens disposed within the elongate body 24 that provide mechanical, electrical and/or fluid communication between the proximal portion 25 and the distal portion 26 of the elongate body 24. In one embodiment, as shown in FIG. 2, the elongate body 24 includes at least one coolant delivery lumen 27, a central lumen 28, and a coolant recovery lumen 29. In some embodiments, the at least one coolant delivery lumen 27 occupies a significantly smaller portion of the cross-sectional area of the elongate body 24 than does the coolant recovery lumen 29. Further, in some embodiments the elongate body 24 does not include guide wire lumen(s) and/or other lumen(s) for steering wires and/or deflection mechanisms. In some embodiments the elongate body 24 may be constructed without a liner (such as a Teflon liner) required in the main lumen. As a result, in some embodiments the cross-sectional area available for the return flow of coolant is increased, while maintaining the same, or approximately the same, outer diameter of the elongate body 24 (for example, 12Fr sheet compatible). Thus, the cross-sectional area of the elongate body 24 available for return flow of coolant is larger than in currently known devices to facilitate recovery of expanded coolant from the balloon(s) 18 to maintain the balloon(s) 18 at a low inflation pressure. In one non-limiting example, the cross-sectional area of the elongate body 24 available for return flow of coolant from the balloon(s) 18 is approximately 0.0059 in$^2$.

Figure 9:
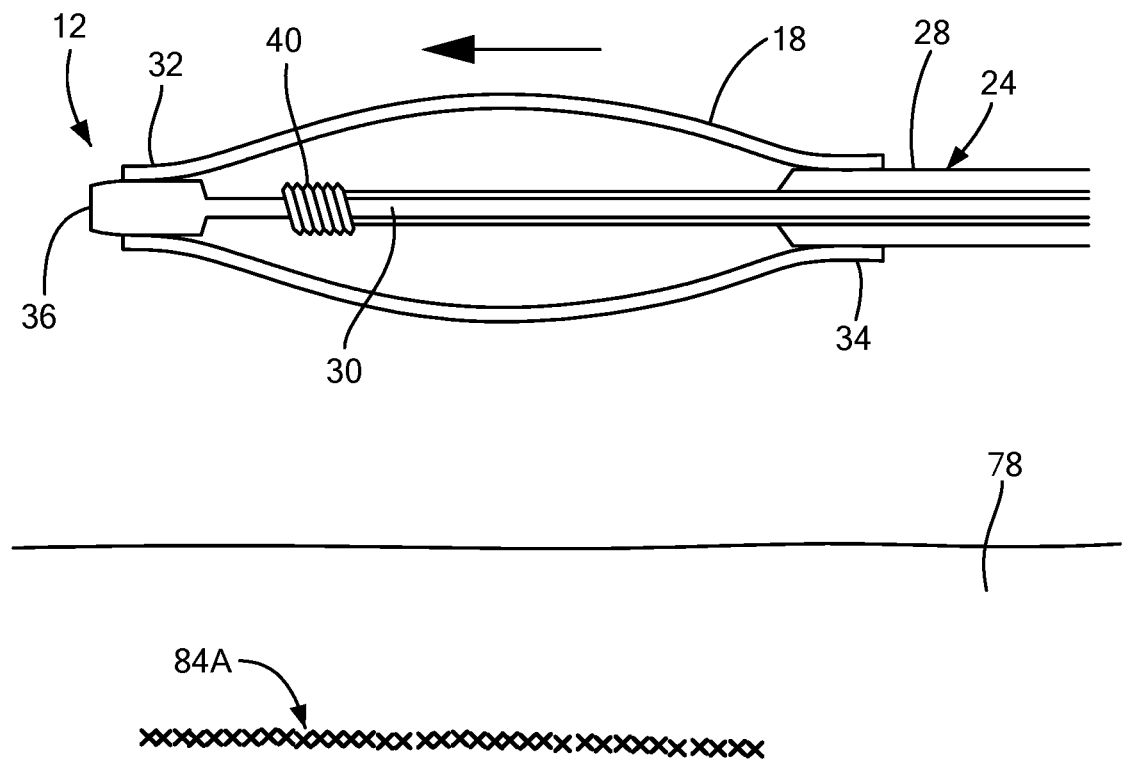
FIG. 9 shows a cross-sectional view of the cryoablation device with the balloon in an extended configuration for creating linear lesions in an area of tissue, in accordance with the present disclosure.
Figure 10:
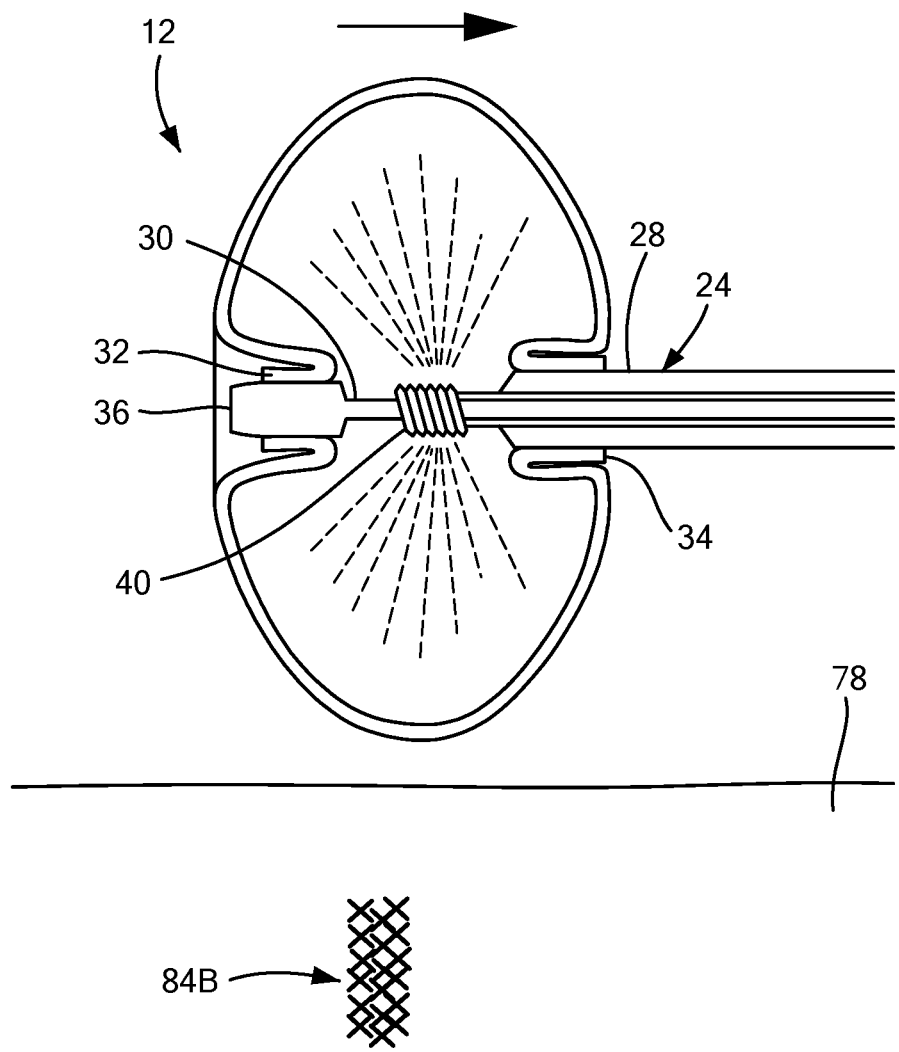
FIG. 10 shows a cross-sectional view of the cryoablation device with the balloon in a retracted configuration for creating focal lesions in an area of tissue, in accordance with the present disclosure.
Figure 11:
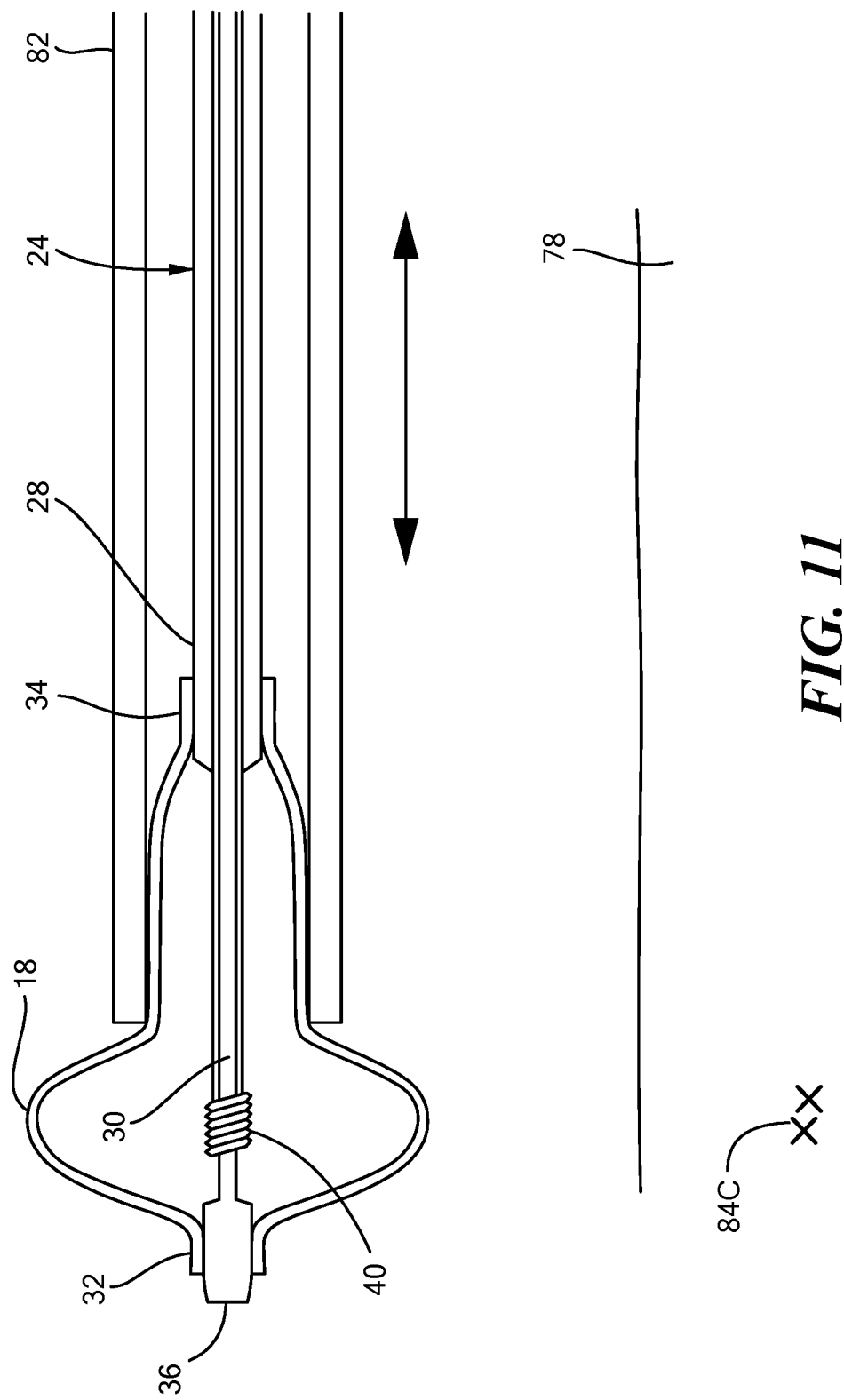
FIG. 11 shows a cross-sectional view of the cryoablation device with the balloon at least partially contained within a sheath, by which expansion of the balloon is restricted, for creating small focal lesions in an area of tissue, in accordance with the present disclosure.

Continuing to refer to FIG. 1, in one embodiment, at least a portion of the treatment element(s) 16 is coupled to the distal portion 26 of the elongate body 24. In one embodiment, the cryoablation device 12 further includes a shaft 30 that is longitudinally movable within the elongate body 24 (for example, within a central lumen of the elongate body 24) such that the shaft is advanceable and retractable within the elongate body 24. In one embodiment, the at least one treatment element 16 includes a balloon 18 having a distal neck 32 and a proximal neck 34, and the distal neck 32 is coupled to a distal tip 36 of the shaft 30 and the proximal neck 34 is coupled to the distal portion 26 of the elongate body 24. In this configuration, movement of the shaft 30 within the elongate body 24 affects the shape and/or configuration of the balloon 18. For example, the shaft 30 may be fully advanced when the balloon 18 is deflated and in a delivery (or first) configuration wherein the balloon 18 has a minimum diameter suitable, for example, for retraction of the cryoablation device 12 within a sheath for delivery to and/or removal from a target treatment site. Conversely, when the balloon 18 is inflated or expanded and in a treatment (or second) configuration, the shaft 30 may be advanced or retracted over a distance that affects the size and/or configuration of the inflated or expanded balloon 18 (as indicated by the double-headed arrow in FIG. 1). In some embodiments, during use of the cryoablation device 12, the shaft 30 is advanced and/or retracted within the elongate body 24 to change the shape of the balloon 18 and, consequently, the ablation pattern (for example, as shown in FIGS. 9-11). Further, the shaft 30 may include a guidewire lumen through which a sensing device, mapping device, guidewire, or other system component may be passed.

Figure 3:
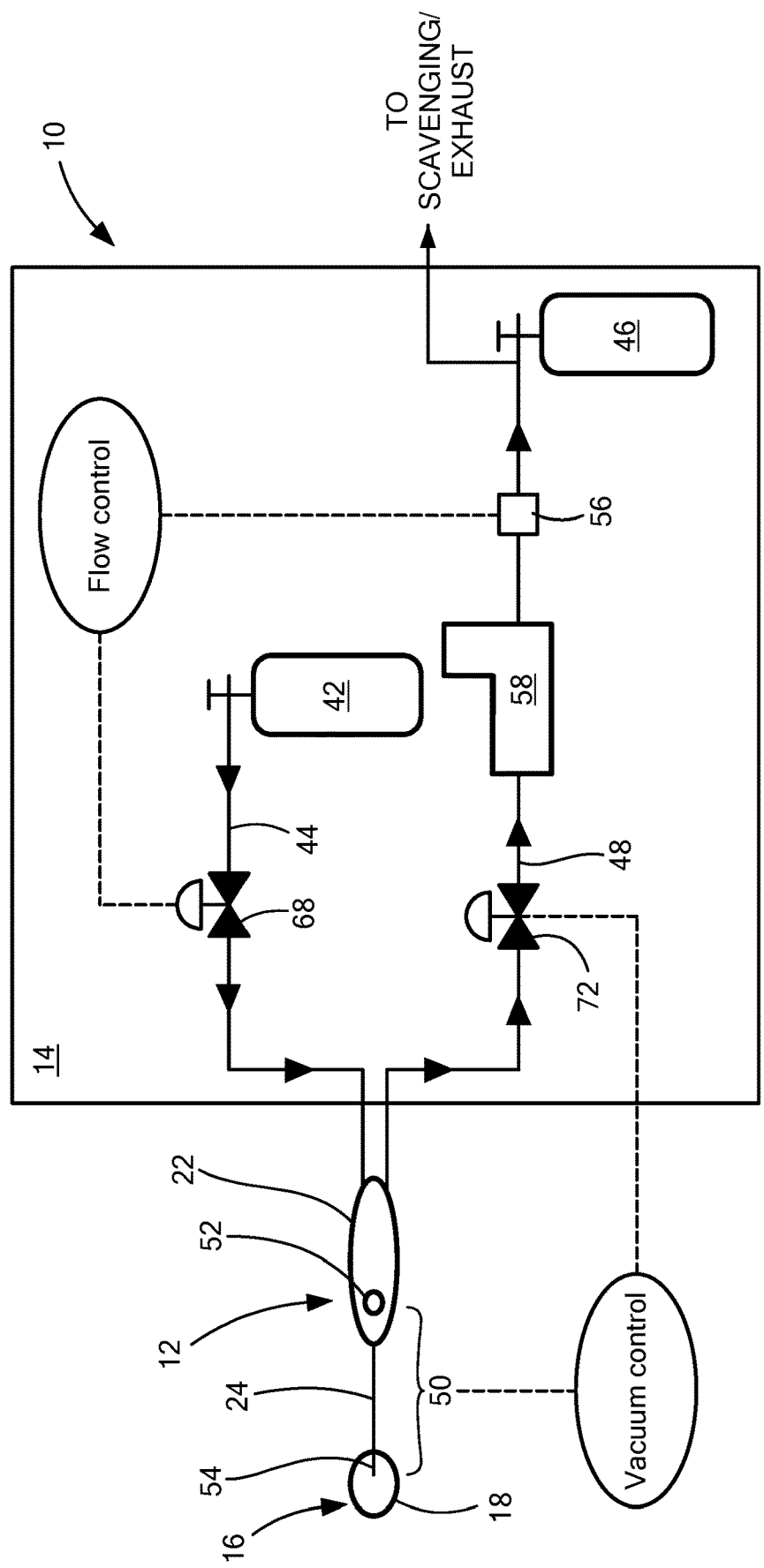
FIG. 3 shows a simplified schematic view of an exemplary fluid flow path through the medical system of FIG. 1, in accordance with the present disclosure.

Continuing to refer to FIG. 1, in one embodiment the balloon 18 defines an interior chamber 38 and the cryoablation device 12 further includes one or more nozzles, orifices, or other fluid delivery elements 40 for delivering fluid, such as coolant, to the interior chamber 38 of the balloon 18. During operation, in one embodiment coolant flows from a coolant supply reservoir 42 through a fluid flow path, including a coolant delivery conduit 44 that is located at least partially within the elongate body 24 of the cryoablation device 12 (for example, as shown in FIG. 3) to the balloon 18. Coolant then enters the interior chamber 38 of the balloon 18, such as through the fluid delivery element(s) 40, after which the coolant cools the balloon 18 before the coolant expands. Expanded coolant then passes from the interior chamber 38 of the balloon 18 to a coolant recovery reservoir 46 and/or scavenging/exhaust system through a coolant recovery conduit 48.

Continuing to refer to FIG. 1, in one embodiment the medical system 10 further includes a sensing system 50 for measuring one or more parameters of operation of the medical system 10. In one embodiment, the sensing system 50 is a pressure sensing system that includes a pressure sensor 52 (for example, a pressure transducer or microelectromechanical sensor (MEMS)) within the handle 22, within the balloon 18, and/or control unit 14 and a pressure sensor extension tube 54 in fluid communication with the pressure sensor 52. In one embodiment, the pressure sensor 52 is located within the handle 22 and the pressure sensor extension tube 54 extends from the pressure sensor 52 to a location within the interior chamber 38 of the balloon 18, and the pressure sensor extension tube 54 includes one or more orifices (not shown) that are configured to be exposed to fluid circulating within the interior chamber 38 when the cryoablation device 12 is in use. Thus, in one embodiment the sensing system 50 is configured to measure a pressure within the interior chamber 38, which correlates to the pressure of the balloon 18. In one embodiment, the sensing system 50 further includes a nitinol tube within at least one lumen of the pressure sensor extension tube 54 to prevent the pressure sensor extension tube 54 from kinking when the elongate body 24 is curved, deformed, or deflected. In one embodiment, the sensing system 50 further includes a flow meter 56 in or in fluid communication with the coolant recovery conduit 48 for measuring the flow of coolant through the coolant recovery conduit 48. In one non-limiting example, the flow meter 56 is located upstream of the coolant recovery reservoir 46. In some embodiments, the cryoablation device 12 and/or the control unit 14 includes one or more additional sensors, such as temperature sensors, flow rate sensors, pressure sensors, impedance sensors, or the like.

Continuing to refer to FIG. 1, in one embodiment the control unit 14 generally includes one or more reservoirs, including the coolant supply reservoir 42, the coolant recovery reservoir 46, and other components of the fluid flow path, such as a vacuum pump 58 for creating a low-pressure environment in one or more conduits of the fluid flow path so that expanded coolant is drawn from the interior chamber 38 of the balloon 18 and toward the proximal portion 25 of the elongate body 24 and into the coolant recovery reservoir 46 and/or scavenging/exhaust system (for example, as shown in FIG. 3). In one non-limiting example, the vacuum pump 58 is located upstream of the flow meter 56 and the coolant recovery reservoir 46. In some embodiments, the control unit 14 also includes an energy generator (not shown). As used herein, the term "control unit" refers to any components of the medical system 10 other than components of the cryoablation device 12 itself, regardless of whether the components are physically located within or external to the control unit 14.

Continuing to refer to FIG. 1, in one embodiment the control unit 14 also includes one or more controllers, processors, and/or software modules containing instructions or algorithms to provide for the automated or semi-automated operation and performance of the features, sequences, or procedures described herein. In one embodiment, the control unit 14 includes a computer 60 having a display 62 and processing circuitry 64 programmed or programmable to execute the automated or semi-automated operation and performance of the features, sequences, calculations, and/or procedures described herein. In one embodiment, the processing circuitry 64 includes a memory and a processor, the memory including instructions that, when executed by the processor, configured the processor to receive, process, or otherwise use signals from the cryoablation device 12 and/or other system components. Additionally, in some embodiments the control unit 14 further includes one or more user input devices 66 (such as a keyboard, touchscreen, keypad, button, knob, or the like), controllers, speakers, and/or displays that are in communication with processing circuitry 64 and used for collecting and conveying information from and to the user.

Referring now to FIG. 3, a simplified schematic view of an exemplary fluid flow path through the medical system 10 is shown. The fluid flow path generally includes a coolant delivery conduit 44 and a coolant recovery conduit 48 (which may also be referred to as a vacuum return line). In one embodiment, the coolant delivery conduit 44 extends from the coolant supply reservoir 42 to interior chamber 38 of the balloon 18 of the cryoablation device 12 and the coolant recovery conduit 48 extends from the interior chamber 38 of the balloon 18 of the cryoablation device 12 to the coolant recovery reservoir 46 and/or a scavenging/exhaust system (or is vented to the atmosphere). In one embodiment, the coolant delivery conduit 44 includes at least one first valve 68 for controlling the flow of coolant through the coolant delivery conduit 44. In one embodiment, the coolant recovery conduit 48 includes a vacuum pump 58 and at least one second valve 72 for controlling the flow of coolant, and thus the balloon expansion pressure, through the coolant recovery conduit 48 and a vacuum pump 58 for providing a low-pressure environment that draws expanded coolant from the interior chamber 38 and into the coolant recovery conduit 48. In one embodiment, the at least one first valve 68 and/or the at least one second valve 72 are proportional valves that are in communication with the control unit 14. Further, in one embodiment, the first valve 68 and/or the second valve 72 is in communication with the sensing system 50 (including the pressure sensor 52, pressure sensor extension tube 54, and flow meter 56). For example, the pressure sensor 52 and/or pressure sensor extension tube 54 are used to measure a pressure within the interior chamber 38 of the balloon 18, and pressure feedback is communicated by the pressure sensor 52 and/or pressure sensor extension tube 54 to the control unit 14. In one embodiment, pressure feedback from the pressure sensor 52 and/or pressure sensor extension tube 54 is communicated to the second valve 72 to adjust or control the vacuum pump 58 and flow of coolant within the coolant recovery conduit 48. Likewise, the flow meter 56 is used to measure a flow of coolant (for example, volume and/or flow rate of coolant) within the coolant recovery conduit 48, and flow feedback is communicated by the flow meter 56 to the control unit 14. In one embodiment, pressure feedback from the flow meter 56 is communicated to the first valve 68 to adjust or control the delivery of coolant from the coolant supply reservoir 42 and flow of coolant within the coolant delivery conduit 44. Each valve 68, 72 is automatically adjusted by the control unit 14 toward an open direction or a closed direction to selectively increase or decrease, respectively, the flow rate of coolant passing through the fluid flow path and/or the balloon expansion pressure.

Figure 4:
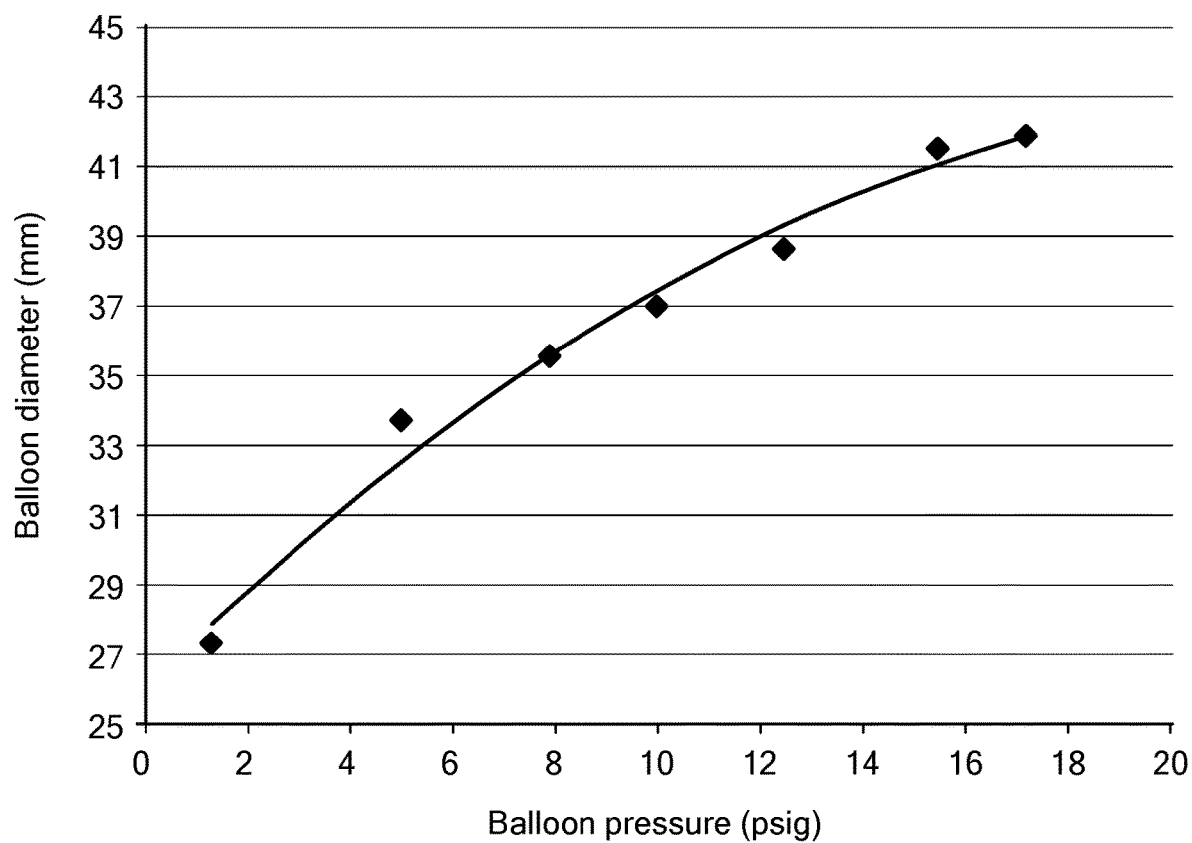
FIG. 4 shows a chart of exemplary data demonstrating a relationship between balloon pressure and balloon size.

Continuing to refer to FIG. 3, and with reference to FIG. 4, in one embodiment, the processing circuitry 64 is configured to provide one or more setpoints, such as flow rate and/or flow volume setpoints, within which the control unit 14 will maintain the flow of coolant through the fluid flow path by automatically adjusting the first and/or second valve 68, 72. In one non-limiting example, the user selects a desired outer diameter of the balloon 18 and inputs that desired outer diameter into the control unit 14, such as by one or more user input devices 66. Put another way, in one embodiment the processing circuitry 64 is configured to receive a target balloon size as input data form the user. The desired outer diameter of the balloon 18 may be chosen based on the tissue being treated, the inner diameter or inner circumference of a hollow anatomical structure within which the balloon 18 will be positioned, the desired ablation area, or the like. For example, the hollow anatomical feature may be a pulmonary vein (PV), and the PV inner diameter may vary from patient to patient, and from PV to PV within a given patient, and the outer diameter of the balloon 18 may be chosen such that the balloon 18 adequately contacts, and can therefore sufficiently ablate, the tissue of the inner surface of the hollow anatomical feature. The user may determine the inner diameter of the hollow anatomical structure based on imaging data, direct visualization, known data for a particular patient, reference data previously obtained, or from other sources, and then select an appropriate balloon size. In one embodiment, processing circuitry 64 is configured to correlate a desired outer diameter of the balloon 18 to a target pressure of the balloon 18. The target pressure of the balloon 18 is the internal pressure of the treatment element 16, for example, the pressure produced within the interior chamber 38 of the balloon 18 by the flow of coolant therein, and this pressure is exerted against the interior surface of the balloon 18 and at least partially determines the firmness or compliancy of the balloon 18. In one embodiment, the target pressure is atmospheric pressure or approximately atmospheric pressure (for example, between −2 psig and +5 psig). As used herein, the pressure of the balloon 18 may refer to pressure during an inflation phase, ablation phase, deflation phase, and/or other phase of a cryoablation procedure. Further, the pressure at each phase of the procedure may be the same or different, as determined by the type of procedure, tissue being treated, size, shape, material, and/or type of treatment element being used, or the like.

Continuing to refer to FIG. 3, in one embodiment, as balloon pressure is directly related to the balloon's size (for example, outer diameter), the processing circuitry 64 is further configured to correlate the pressure to a coolant flow rate through the fluid flow path. For example, as shown in FIG. 4 (data shown is for a single polyurethane balloon), the outer diameter of the balloon 18 may increase with an increase in pressure and may decrease with a decrease in pressure. In one embodiment, the outer diameter of the balloon 18 may be adjusted to be between approximately 25 mm and approximately 38 mm (±2 mm). In one embodiment, the outer diameter of the balloon 18 may be adjusted to be between approximately 25 mm and approximately 35 mm (±2 mm). Further, in one embodiment the balloon 18 is operable at any of a variety of pressures, including a low pressure of less than approximately −15 psig under vacuum to 10 psig when inflated, and including a low pressure that is equal to or approximately equal to atmospheric pressure (for example, between −2 psig and +5 psig). In one embodiment, cryoablation is performed with a balloon 18 that is maintained at a low pressure, as this makes the balloon 18 more compliant and conformable to a variety of tissue shapes and configurations. Additionally, a more compliant balloon may allow for cryoablation over a larger area of tissue, as the contact surface area 76 of the balloon may increase when pressed against the tissue.

Additionally, the cooling power of the balloon 18 (that is, the balloon's capacity to remove heat from adjacent tissue or blood) is proportional to the balloon's size. As such, continuing to refer to FIG. 3, in one embodiment the processing circuitry 64 is further configured to not only determine a target balloon pressure, but also to determine the optimal coolant flow rate for the selected balloon size. As discussed above, in one embodiment, the user selects a desired outer diameter of the balloon 18 and inputs that desired outer diameter into the control unit 14, such as by one or more user input devices 66. Based on the desired or target balloon size (for example, outer diameter), the processing circuitry 64 is configured to determine a target pressure using the known relationship between balloon pressure and size/outer diameter, as well as a target coolant flow rate to achieve and/or maintain the target balloon pressure and the required cooling capacity (or cooling power) for creating lesions in the area of tissue with the cryoablation device 12. In one embodiment, the processing circuitry 64 is programmed to then determines corresponding flow rate setpoints for maintaining the target balloon pressure. For example, in one embodiment the processing circuitry 64 is programmed to determine a minimum flow rate setpoint and a maximum flow rate setpoint. If a measured flow rate falls below the minimum flow rate setpoint or rises above the maximum flow rate setpoint, the processing circuitry 64 adjusts the valve(s) 68, 72 to increase or decrease the flow of coolant through the fluid flow path to bring the balloon pressure back to the target pressure. Additionally or alternatively, the processing circuitry 64 is programmed to adjust one or more other valves or components of the medical system 10 bring the balloon pressure back to the target pressure. Thus, the processing circuitry 64 controls the pressure to inflate the balloon 18 to the desired size and, once ablation is initiated, maintains balloon pressure, and, therefore, the size, of the balloon 18 throughout the procedure or until changed by the user.

Figure 5:
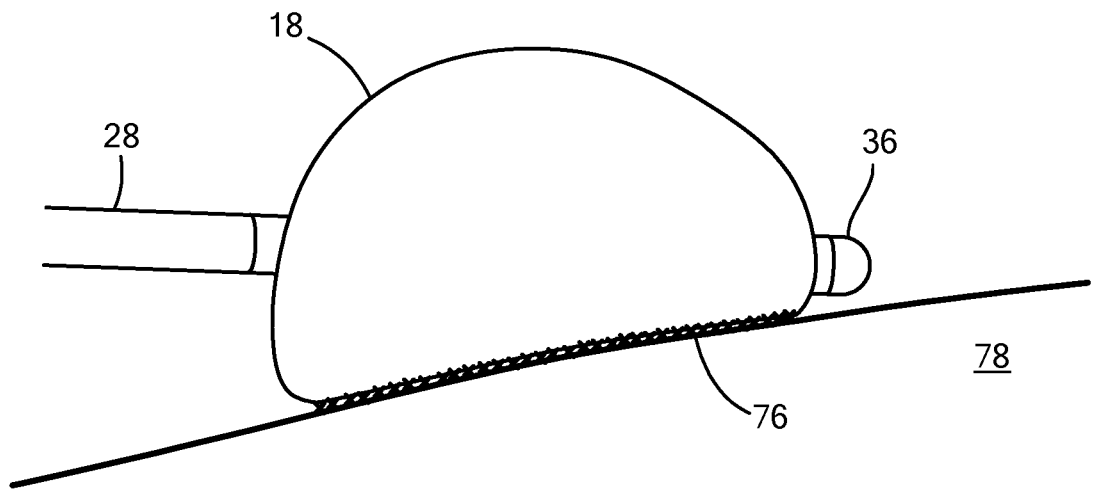
FIG. 5 shows a first side view of the cryoablation device with the balloon positioned in contact with an area of tissue, in accordance with the present disclosure.
Figure 6:
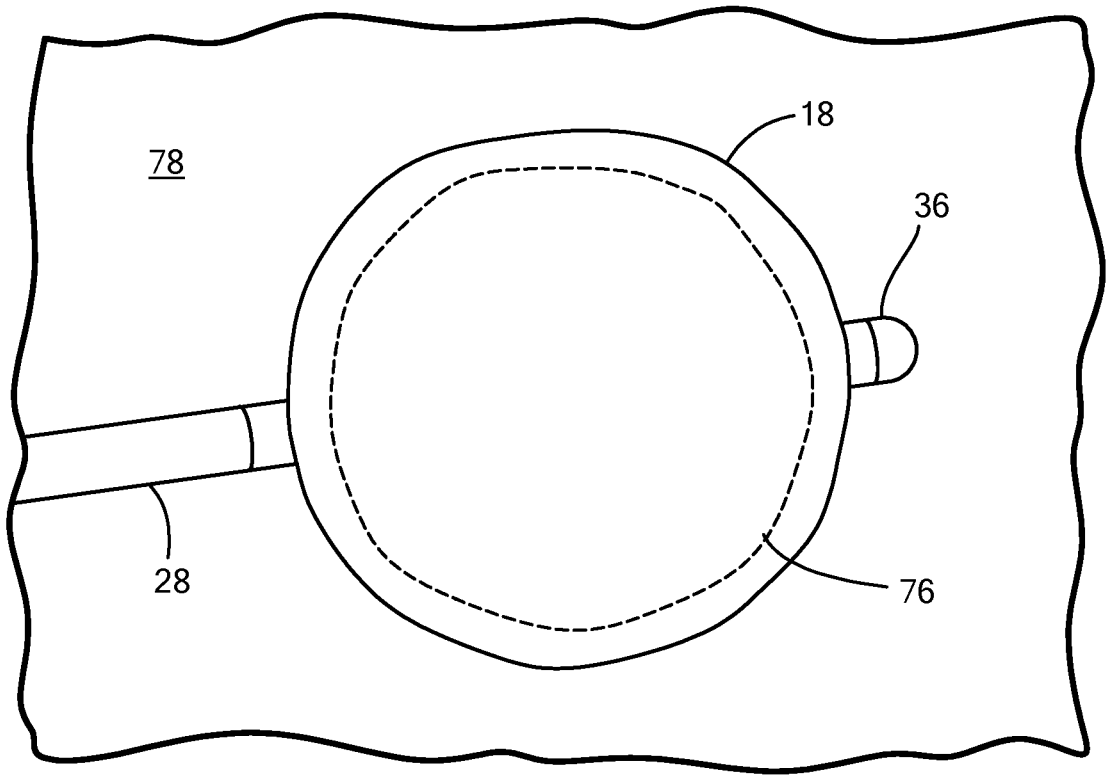
FIG. 6 shows a second side view of the cryoablation device of FIG. 5 with the balloon positioned in contact with the area of tissue, in accordance with the present disclosure.

Referring now to FIGS. 5 and 6, a distal portion of a cryoablation device 12 with a balloon 18 positioned in contact with an area of tissue 78 is shown. As shown in FIGS. 5 and 6, the balloon 18 is inflated to a low pressure such that the balloon 18 has a wider contact surface area when pressured against the tissue 78 than a balloon that is fully inflated to a higher pressure. FIG. 5 shows a first side view of the balloon 18 of the cryoablation device 12 and FIG. 6 shows a second side view of the balloon 18 of the cryoablation device 12.

Figure 7:
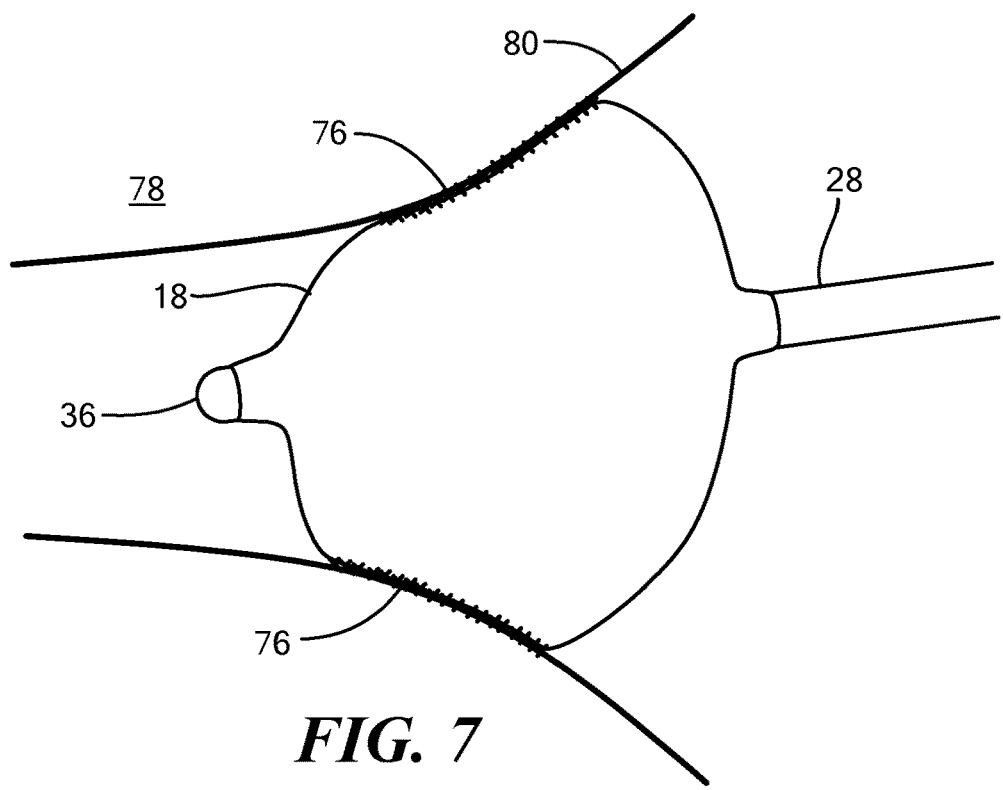
FIG. 7 shows the cryoablation device with the balloon positioned within a hollow anatomical structure (for example, a pulmonary vein), in accordance with the present disclosure.
Figure 8:
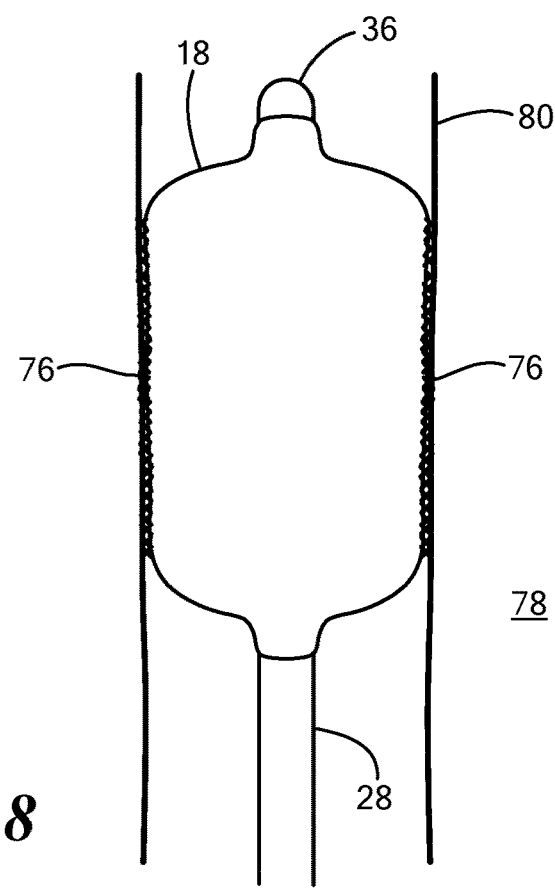
FIG. 8 shows the cryoablation device with the balloon positioned within a hollow anatomical structure (for example, a renal artery), in accordance with the present disclosure.

Referring now to FIGS. 7 and 8, a distal portion of a cryoablation device 12 with a balloon 18 positioned relative to a hollow anatomical structure 80 is shown. In one embodiment, the hollow anatomical structure 80 is one of a vein and an artery, such as a pulmonary vein (PV), a renal artery, a carotid artery, or the like. FIG. 7 shows the balloon 18 of the cryoablation device 12 positioned such that at least a portion of the balloon 18 is within a PV and in contact with the PV ostium and/or PV antrum. FIG. 8 shows the balloon 18 of the cryoablation device 12 positioned entirely within a hollow anatomical structure 80 such as a renal artery, the balloon 18 being in contact with the inner circumference of the hollow anatomical structure 80. As discussed above, the size and, therefore, the pressure of the balloon 18 may be chosen according to the inner diameter (or inner circumference) of the hollow anatomical structure 80.

Referring now to FIGS. 9-11, the distal portion of a cryoablation device 12 is shown, with a balloon 18 positioned relative to an area of tissue 78 and the balloon 18 in exemplary ablation configurations. In addition to controlling flow rate to maintain the balloon 18 at a target or selected size based on the configuration of the target area of tissue, the size and shape of the balloon 18 may be physically manipulated by the user to create a desired ablation pattern. FIG. 9 shows the balloon 18 in an extended configuration for creating linear lesions; FIG. 10 shows the balloon 18 in a retracted configuration for creating focal (or slightly linear) lesions; and FIG. 11 shows the balloon 18 at least partially contained within a sheath 82 for creating small focal lesions.

Referring to FIGS. 9 and 10, in some embodiments the configuration of the balloon 18 and, therefore, the resulting ablation pattern, is at least partially controlled by advancement and retraction of the shaft 30 within the elongate body 24. As shown in FIG. 9, advancement of the shaft 30 distally within the elongate body 24 (as indicated by the distally facing arrow in FIG. 9) causes the balloon 18 to transition to an extended configuration in which the balloon 18 has an elongate shape. In this extended configuration, circulation of coolant through the balloon 18 allows the balloon 18 to create linear lesions 84A in an area of tissue 78 with which the balloon 18 is in contact. Conversely, as shown in FIG. 10, retraction of the shaft 30 proximally within the elongate body 24 (as indicated by the proximally facing arrow in FIG. 10) causes the balloon 18 to transition to a retracted configuration in which the balloon 18 has a shortened shape with a larger equator (or maximum outer diameter). Additionally, in some embodiments retraction of the shaft 30 aligns the fluid delivery element(s) 40 with the equator of the balloon 18, thereby allowing the balloon 18 to create focal lesions (or slightly linear lesions) 84B in an area of tissue 78 with which the balloon 18 is in contact when coolant is circulated through the balloon 18. In FIGS. 9 and 10, the cryoablation device 12 is shown in cross-section and adjacent an area of tissue. It is noted that the area of tissue is not shown in plain view so an exemplary ablation pattern can be seen.

Referring to FIG. 11, in one embodiment the configuration of the balloon and, therefore, the resulting ablation pattern, is at least partially controlled by advancement and retraction of a sheath 82 over the outside of the balloon 18 to conceal at least a portion of the balloon 18. As indicated by the double-headed arrow in FIG. 11, in one embodiment the sheath 82 is advanceable and retractable over the outside of the cryoablation device 12. In one embodiment, the sheath 82 is advanceable over the balloon 18 so only a distal portion of the balloon 18 may be exposed from the sheath 82. In this configuration, the exposed portion of the balloon 18 may be used to create a focal lesion 84C in an area of tissue with which the balloon 18 is in contact. Further, the amount of the balloon 18 exposed from the sheath 82 determines the size of the focal lesion, as the sheath 82 thermally insulates the portion of the balloon 18 within the sheath 82, thus at least partially shielding the tissue 78 from cryoablation. Thus, in one exemplary method of use the user advances the sheath 82 over the balloon 18 until an amount of the balloon 18 is exposed that will create a focal lesion of a desired size.

Figure 12:
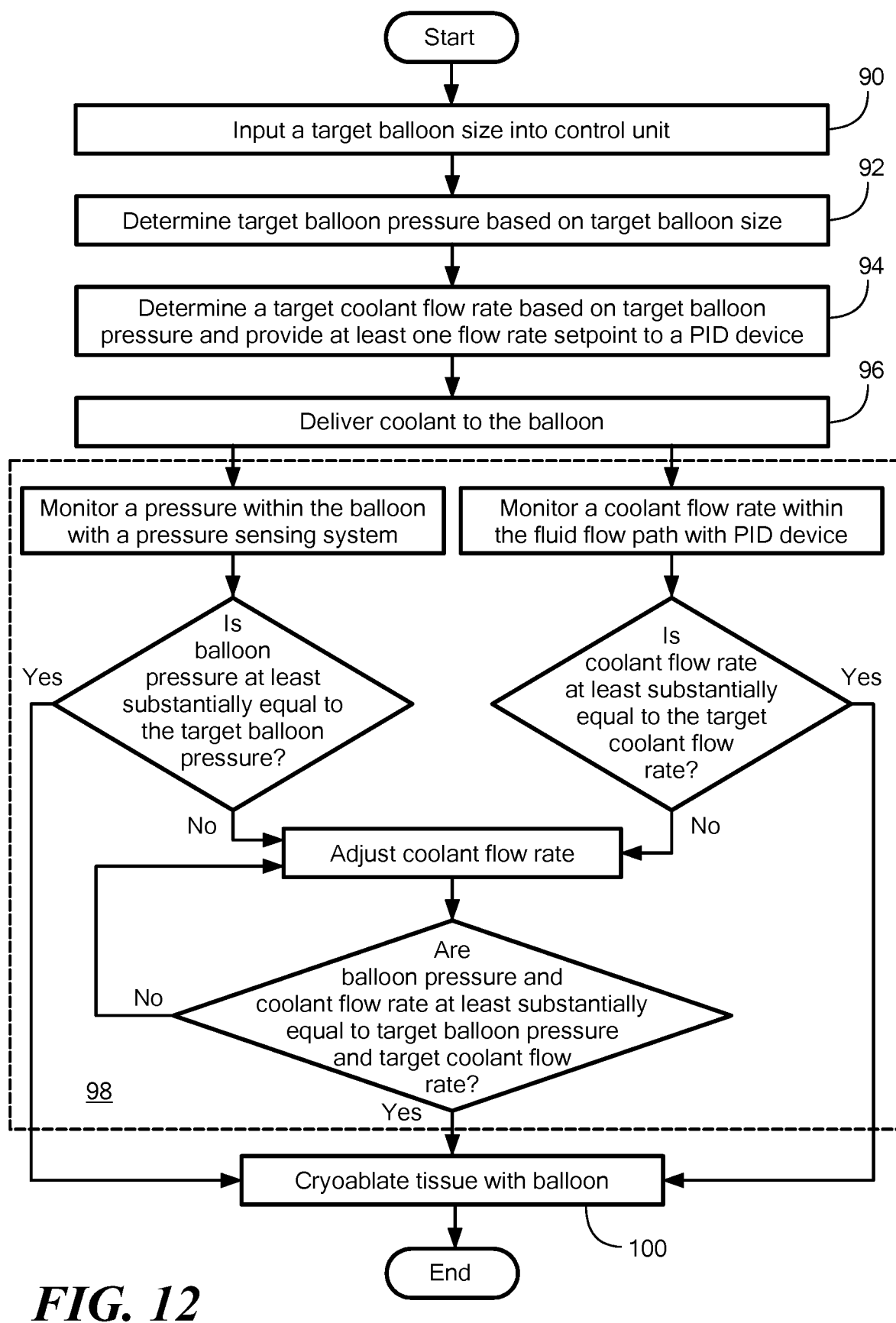
FIG. 12 shows a flow chart of an exemplary method of ablating tissue using a cryoablation device with a balloon.

Referring now to FIG. 12, a flow chart of an exemplary method of ablating tissue using a cryoablation device 12 with a balloon 18 is shown. In a first step 90, a user selects a desired or target size (for example, outer diameter) of the balloon 18 and inputs that desired size into the control unit 14, such as by one or more user input devices 66. For example, the desired outer diameter of the balloon 18 may be chosen based on the tissue being treated, the inner diameter or inner circumference of a hollow anatomical structure 80 within which the balloon 18 will be positioned, the desired ablation area, or the like. Further, the user may determine the inner diameter or inner circumference of the of the hollow anatomical structure 80 based on imaging data, direct visualization, known data for a particular patient, reference data previously obtained, or from other sources, and then select an appropriate balloon size based on the determined inner diameter/circumference of the hollow anatomical structure 80.

Continuing to refer to FIG. 12, in a second step 92 the processing circuitry 64 determines a target balloon pressure based on the desired or target balloon size chosen by the user. In a third step 94, the processing circuitry 64 is programmed to determine a target coolant flow rate based on the target balloon pressure and generates one or more flow rate setpoints for maintaining the target balloon pressure. In one embodiment, the processing circuitry 64 is programmed to determine the target coolant flow rate to ensure that the flow of coolant through the interior chamber 38 of the balloon 18 provides the balloon 18 with sufficient cooling capacity to ablate an area of tissue adjacent/in contact with the balloon 18, regardless of the balloon pressure. That is, in one embodiment the processing circuitry 64 is configured to select a target cooling capacity of the balloon 18 that is sufficient to allow the balloon 18 to cryoablate tissue even if the balloon pressure is low. Optionally, the user may change or adjust the shape of the balloon 18, such as by advancing or retracting the shaft 30 and/or advancing or retracting a sheath 82 at least partially over the balloon 18.

Continuing to refer to FIG. 12, in a fourth step 96 the processing circuitry 64 initiates or continues a delivery of coolant to the interior chamber 38 of the balloon 18. In a fifth step 98, the processing circuitry 64 continues to monitor the pressure within the interior chamber 38 of the balloon 18 and/or the flow of coolant through the coolant recovery conduit 48 to ensure the balloon pressure is maintained at (that is, at least substantially equal to) the target balloon pressure. In one embodiment, the processing circuitry 64 is in communication with and receives pressure data from a pressure sensor 52 and/or a pressure sensor extension tube 54 at least partially located within the interior chamber 38 of the balloon 18 and/or from a flow meter 56 in or in fluid communication with the coolant recovery conduit 48. In one embodiment, if the pressure rises above or falls below the target balloon pressure, in one embodiment the processing circuitry 64 is programmed to adjust one or more valves or other components of the medical system 10 to adjust the flow of coolant through the fluid flow path to bring the balloon pressure back to the target balloon pressure. Further, in one embodiment the coolant flow may be monitored by the processing circuitry 64 based on data from the flow meter 56. In a sixth step 100, once the processing circuitry 64 determines the balloon pressure and coolant flow rate are at least substantially equal to the target balloon pressure and target fluid flow rate, this is communicated to the user and the user initiates or continues cryoablation of the target tissue with the cryoablation device 12. Thus, in one embodiment the sensing system 50, the processing circuitry 64 creates a feedback loop for maintaining the size of the balloon during the procedure. Likewise, in some embodiments the processing circuitry 64 is programmed to monitor the coolant flow rate to maintain the coolant flow rate such that the balloon 18 is maintained at the target balloon size and the target cooling capacity of the balloon 18 is maintained.

Embodiments

In one embodiment, a cryoablation system 10 comprises: a cryoablation device 12, the cryoablation device 12 including: an expandable treatment element 18 defining an interior chamber 38; and a pressure sensing system 50 at least partially within the interior chamber 38; a fluid flow path, the fluid flow path including at least one valve 68, 72; and a control unit 14, the control unit 14 including processing circuitry 64 in communication with the pressure sensing system 50, the processing circuitry 64 being configured to: determine a target pressure of the expandable treatment element 18 based on a target size of the expandable treatment element 18; and determine a target flow rate of coolant through the fluid flow path based on the target pressure of the expandable treatment element 18.

In one aspect of the embodiment, the fluid flow path includes a coolant delivery conduit 44 and a coolant recovery conduit 48. In one aspect of the embodiment, the coolant delivery conduit 44 includes a first valve 68. In one aspect of the embodiment, the coolant recovery conduit 48 includes a second valve 72.

In one aspect of the embodiment, the processing circuitry 64 is further configured to: determine at least one flow rate setpoint and adjust the at least one valve 68, 72 to maintain a flow rate of coolant through the fluid flow path at the target flow rate.

In one aspect of the embodiment, the processing circuitry 64 is configured to determine the target flow rate of coolant through the fluid flow path based on the target pressure of the expandable treatment element 18 and a target cooling capacity of the expandable treatment element 18. In one aspect of the embodiment, the target cooling capacity is one at which the expandable treatment element 18 is operable to ablate tissue. In one aspect of the embodiment, the target pressure is at most 10 psig.

In one aspect of the embodiment, the processing circuitry 64 is further configured to receive the target size of the expandable treatment element 18 as input data from a user. In one aspect of the embodiment, the target size of the expandable treatment element 18 is between approximately 25 mm and approximately 38 mm.

In one aspect of the embodiment, the pressure sensing system 50 includes: a pressure sensor 52; and a pressure sensor extension tube 54 in fluid communication with the pressure sensor 52.

In one aspect of the embodiment, the pressure sensing system further includes a flow meter in fluid communication with the fluid flow path.

In one aspect of the embodiment, the cryoablation device 12 further includes: an elongate body 24 having a distal portion 26 and a proximal portion 25 opposite the distal portion 26, the expandable treatment element 18 being coupled to the distal portion 26; and a handle 22 coupled to the proximal portion 25, the pressure sensor 52 being located within the handle 22 and the pressure sensor extension tube 54 extending through the elongate body 24 such that at least a portion of the pressure sensor extension tube 54 is located within the interior chamber 38 of the expandable treatment element 18.

In one embodiment, a cryoablation system 10 comprises a control unit 14 including processing circuitry 64, the processing circuitry 64 being configured to: receive a target size of an expandable treatment element 18 of a cryoablation device 12 as input data from a user; determine a target pressure of the expandable treatment element 18 based on a target size of the expandable treatment element 18; and determine a target flow rate of coolant through the fluid flow path based on the target pressure of the expandable treatment element 18 and a target cooling capacity of the expandable treatment element 18.

In one aspect of the embodiment, wherein the target pressure is at most 10 psig.

In one aspect of the embodiment, the target size of the expandable treatment element 18 is between approximately 25 mm and approximately 38 mm.

In one aspect of the embodiment, the target cooling capacity is one at which the expandable treatment element 18 is operable to ablate tissue.

In one embodiment, a method of cryoablating tissue comprises: inputting into a control unit 14 a target balloon size, the control unit 14 including processing circuitry 64, the target balloon size being the target size of a balloon 18 of a cryoablation device 12; determining, with the processing circuitry 64, a target balloon pressure based on the target balloon size; determining, with the processing circuitry 64, a target coolant flow rate based on the target balloon pressure and a target cooling capacity of the balloon 18; delivering coolant through a fluid flow path to the balloon 18; maintaining the target coolant flow rate through a cryoablation procedure, such that the target balloon size, target balloon pressure, and target cooling capacity are maintained; and cryoablating tissue with the balloon 18.

In one aspect of the embodiment, the processing circuitry 64 is in communication with a valve 68, 72 in the fluid flow path 44, 48, the step of maintaining the target coolant flow rate including: determining, with the processing circuitry 64, at least one flow rate setpoint; and automatically adjusting the valve 68, 72 to maintain a flow of coolant through the fluid flow path 44, 48 at the target flow rate. In one aspect of the embodiment, the method further comprises: measuring a pressure within the balloon 18 with a pressure sensing system 50; comparing the measured pressure with the target balloon pressure; and automatically adjusting the flow of coolant through the fluid flow path 44, 48 to adjust the measured pressure to the target balloon pressure.

In one aspect of the embodiment, the method further comprises: positioning the balloon 18 at least partially within a hollow anatomical structure 80, the target balloon size being a size that allows the balloon 18 to be in contact with an inner surface of the hollow anatomical structure 80; and cryoablating the inner surface of the hollow anatomical structure 80.

The details of one or more aspects of the disclosure are set forth in the accompanying drawings and the description below. Other features, objects, and advantages of the techniques described in this disclosure will be apparent from the description and drawings, and from the claims.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A cryoablation system comprising:
a cryoablation device, the cryoablation device including:
an expandable treatment element defining an interior chamber; and
a pressure sensing system at least partially within the interior chamber;
a fluid flow path, the fluid flow path including at least one valve; and
a control unit, the control unit including processing circuitry in communication with the pressure sensing system, the processing circuitry configured to:
receive a target size of an expandable treatment element of a cryoablation device as input data from a user;
determine a target pressure of the expandable treatment element based on the target size of the expandable treatment element;
determine a target flow rate of coolant through the fluid flow path based on the target pressure of the expandable treatment element; and
automatically adjust the at least one valve to maintain a flow rate of coolant through the fluid flow path according to the target flow rate.

2. The cryoablation system of claim 1, wherein the fluid flow path includes a coolant delivery conduit and a coolant recovery conduit.

3. The cryoablation system of claim 2, wherein the coolant delivery conduit includes a first valve.

4. The cryoablation system of claim 3, wherein the coolant recovery conduit includes a second valve.

5. The cryoablation system of claim 1, wherein the processing circuitry is further configured to:
determine at least one flow rate setpoint and adjust the at least one valve to maintain a flow rate of coolant through the fluid flow path at the target flow rate according to the at least one flow rate setpoint.

6. The cryoablation system of claim 1, wherein the processing circuitry is configured to determine the target flow rate of coolant through the fluid flow path based on the target pressure of the expandable treatment element and a target cooling capacity of the expandable treatment element.

7. The cryoablation system of claim 6, wherein the target cooling capacity is one at which the expandable treatment element is operable to ablate tissue.

8. The cryoablation system of claim 7, wherein the target pressure is at most 10 psig.

9. The cryoablation system of claim 1, wherein the processing circuitry is further configured to receive the target size of the expandable treatment element as input data from a user.

10. The cryoablation system of claim 9, wherein the target size of the expandable treatment element is between approximately 25 mm and approximately 38 mm.

11. The cryoablation system of claim 1, wherein the pressure sensing system includes:
a pressure sensor; and
a pressure sensor extension tube in fluid communication with the pressure sensor.

12. The cryoablation system of claim 11, wherein the pressure sensing system further includes a flow meter in fluid communication with the fluid flow path.

13. The cryoablation system of claim 11, wherein the cryoablation device further includes:
an elongate body having a distal portion and a proximal portion opposite the distal portion, the expandable treatment element being coupled to the distal portion; and
a handle coupled to the proximal portion,
the pressure sensor being located within the handle and the pressure sensor extension tube extending through the elongate body such that at least a portion of the pressure sensor extension tube is located within the interior chamber of the expandable treatment element.

14. The cryoablation system of claim 1, wherein the target size of the expandable element is determined based on a physical characteristic of a tissue to be ablated.

15. A cryoablation system comprising a control unit including processing circuitry, the processing circuitry configured to:
receive a target size of an expandable treatment element of a cryoablation device as input data from a user;
determine a target pressure of the expandable treatment element based on a target size of the expandable treatment element;
determine a target flow rate of coolant through a fluid flow path based on the target pressure of the expandable treatment element and a target cooling capacity of the expandable treatment element; and
automatically adjust at least one valve to maintain a flow rate of coolant through the fluid flow path according to the target flow rate.

16. The cryoablation system of claim 15, wherein the target pressure is at most 10 psig.

17. The cryoablation system of claim 16, wherein the target size of the expandable treatment element is between approximately 25 mm and approximately 38 mm.

18. The cryoablation system of claim 15, wherein the target cooling capacity is one at which the expandable treatment element is operable to ablate tissue.

19. A method of cryoablating tissue, the method comprising:
inputting into a control unit a target balloon size, the control unit including processing circuitry, the target balloon size being the target size of a balloon of a cryoablation device;
determining, with the processing circuitry, a target balloon pressure based on the target balloon size;
determining, with the processing circuitry, a target coolant flow rate based on the target balloon pressure and a target cooling capacity of the balloon;
delivering coolant through a fluid flow path to the balloon;

automatically adjusting at least one valve of the fluid flow path to-maintain the target coolant flow rate through a cryoablation procedure, such that the target balloon size, target balloon pressure, and target cooling capacity are maintained; and cryoablating tissue with the balloon.

20. The method of claim 19, wherein the processing circuitry is in communication with a valve in the fluid flow path, the step of maintaining the target coolant flow rate including:

determining, with the processing circuitry, at least one flow rate setpoint; and automatically adjusting the valve to maintain the flow rate of coolant through the fluid flow path at the target flow rate according to the at least one flow rate setpoint.

21. The method of claim 20, further comprising:

measuring a pressure within the balloon with a pressure sensing system;

comparing the measured pressure with the target balloon pressure; and automatically adjusting the flow of coolant through the fluid flow path to adjust the measured pressure to the target balloon pressure.

22. The method of claim 19, further comprising:

positioning the balloon at least partially within a hollow anatomical structure, the target balloon size being a size that allows the balloon to be in contact with an inner surface of the hollow anatomical structure; and cryoablating the inner surface of the hollow anatomical structure.

* * * * *